(12) United States Patent
Feldman et al.

(10) Patent No.: US 11,553,902 B2
(45) Date of Patent: Jan. 17, 2023

(54) DEVICE FOR ASSESSING COLON CLEANLINESS

(71) Applicant: Funds For Medical Research Development Of Infrastructure & Health Services, Barzilai Medical Center, Ashkelon (IL)

(72) Inventors: Arie Feldman, Ashkelon (IL); Jacov Blank, Ramat Hasharon (IL)

(73) Assignee: FUNDS FOR MEDICAL RESEARCH DEVELOPMENT OF INFRASTRUCTURE & HEALTH SERVICES, BARZILAI MEDICAL CENTER

(*) Notice: Subject to any disclaimer, the term of this patent is extended or adjusted under 35 U.S.C. 154(b) by 159 days.

(21) Appl. No.: 17/044,834

(22) PCT Filed: Apr. 2, 2019

(86) PCT No.: PCT/IL2019/050382
§ 371 (c)(1),
(2) Date: Oct. 1, 2020

(87) PCT Pub. No.: WO2019/193593
PCT Pub. Date: Oct. 10, 2019

(65) Prior Publication Data
US 2021/0128120 A1    May 6, 2021

(30) Foreign Application Priority Data
Apr. 3, 2018  (IL) ........................................ 258490

(51) Int. Cl.
*G06T 7/00*     (2017.01)
*A61B 10/00*    (2006.01)
*G06T 7/90*     (2017.01)
*A61B 1/31*     (2006.01)

(52) U.S. Cl.
CPC ........ *A61B 10/0038* (2013.01); *G06T 7/0012* (2013.01); *G06T 7/90* (2017.01); *A61B 1/31* (2013.01); *G06T 2207/10024* (2013.01)

(58) Field of Classification Search
CPC ..... A61B 10/0038; A61B 1/31; A61B 5/1034; A61B 5/4255; G06T 7/0012; G06T 7/90; G06T 2207/10024
See application file for complete search history.

(56) References Cited

U.S. PATENT DOCUMENTS

| 2009/0305331 A1 | 12/2009 | Ben-Horin et al. |
| 2017/0303901 A1 | 10/2017 | Sekine |
| 2018/0271501 A1 | 9/2018 | Wang |

FOREIGN PATENT DOCUMENTS

| WO | WO2008/102340 A2 | 8/2008 | |
| WO | WO-2009140764 A1 * | 11/2009 | ........... A61K 31/194 |
| WO | WO2017/049516 A1 | 3/2017 | |

OTHER PUBLICATIONS

International Search Report and Written Opinion for corresponding International application No. PCT/IL2019/050382; dated Jul. 10, 2019 (11 pages).

* cited by examiner

*Primary Examiner* — Siamak Harandi
(74) *Attorney, Agent, or Firm* — Mendelsohn Dunleavy, P.C.

(57) ABSTRACT

A colon cleanliness indicating device including a forward toilet-secured receiving section configured with a recessed receptacle for receiving colonic effluent and a rearward indicating section for indicating a degree of colon cleanliness. The indicating section is formed with one or more channels in fluid communication with the receptacle through which the received colonic effluent is flowable and by which the received colonic effluent can be visualized in order to assess a degree of colon cleanliness.

19 Claims, 7 Drawing Sheets

DEVICE FOR ASSESSING COLON CLEANLINESS

FIELD OF THE INVENTION

The present invention relates to the field of invasive screening. More particularly, the invention relates to a device for assessing colon cleanliness prior to performance of a colonoscopy.

BACKGROUND OF THE INVENTION

Colonoscopy is an important test made in order to explore the health of the colon, in order to detect colon diseases, for example cancer. Colorectal cancer (CRC) is the third most common cancer worldwide. The incidence of colorectal cancer has been effectively reduced in patients who have undergone colonoscopy.

A colonoscopy is an endoscopic visual examination of the interior of the colon, whereby preferably all colonic and rectal mucosa is examined and the cecum is reached, and grants the opportunity for biopsy or removal of suspected colorectal cancer lesions. Polyps as small as 1 mm or less can be removed during the colonoscopy procedure and be evaluated to determine whether they are precancerous.

The efficacy of a colonoscopy is dependent on the degree of colon cleanliness, generally related to a lack of solid matter, in order to enable proper visualization of the mucosa. Methods have been developed whereby bowel preparations comprised of laxative and other cleaning agents are ingested in the comfort of one's home to empty the colon. Many times, however, patients fail to comply with the colonoscopy preparation instructions. As a result, some pathological lesions are missed during the colonoscopy, or the procedure is cancelled or repeated due to poor stool quality. The cost to health facilities due to repeat procedures resulting from inadequate compliance with the colonoscopy preparation instructions is substantial.

It would therefore be desirable to provide objective means for assessing the degree of colon cleanliness prior to performance of a colonoscopy in order to avoid the costs of a cancelled or repeated procedure.

WO 2008/102340 discloses a method and kit for determining a cleanliness level of a colon by determining a parameter associated with colon cleanliness in a sample obtained from the subject and associating the parameter with the cleanliness level of the colon of the subject. A funnel directs a sample of colonic effluent to a container. In one embodiment, a qualitative color scale is provided as an indicator of cleanliness in the sample.

Although the subject is able to assess for himself or for herself the level of colon cleanliness, the results of the assessment are not readily available to the health facility. The health facility will either have to rely on the subject's judgment to determine whether the colonoscopy should proceed, knowing that there exists a distinct possibility of subject error and that the procedure may have to be cancelled or repeated, or require the subject to transport the sample to the health facility by a distasteful and logistically difficult operation, which is not practical.

It is an object of the present invention to provide a device for objectively assessing a degree of colon cleanliness, and therefore a degree of patient readiness to undergo a colonoscopy.

It is an additional object of the present invention to provide a device for validating a degree of colon cleanliness.

Other objects and advantages of the invention will become apparent as the description proceeds.

SUMMARY OF THE INVENTION

A colon cleanliness indicating device comprises a forward toilet-secured receiving section configured with a recessed receptacle for receiving colonic effluent and a rearward indicating section for indicating a degree of colon cleanliness, wherein said indicating section is formed with one or more channels in fluid communication with said receptacle through which said received colonic effluent is flowable and by which said received colonic effluent is able to be visualized in order to assess a degree of colon cleanliness.

Each of the one or more channels is configured with an internal gap of a sufficiently small dimension to induce flow therethrough of the received colonic effluent by capillary action, which is of great utility since the indicating section is generally angularly spaced with respect to the receiving section, and particularly the indicating section is substantially vertically oriented.

The indicating section is preferably made of transparent or translucent material to facilitate visualization of the induced-flow colonic effluent. The indicating section may be provided with a color scale to facilitate comparison of a color of the visualized induced-flow colonic effluent with a range of reference colors displayed on the scale.

In one embodiment, each of the one or more channels is made from two separated material layers, wherein one of said two layers is formed with an aperture to define an opening of the colonic effluent receptacle. The two layers are preferably unseparated within the receiving section forwardly of the aperture, and also within portions of the receiving section that are laterally spaced from the aperture.

In one aspect, the indicating section is partitioned to define a plurality of laterally adjacent channels. Each partition between a pair of the laterally adjacent channels is connected to the two layers along the entire length of the indicating section and along a rearward portion of the receiving section to an edge of the aperture. An insert is insertable within a corresponding one of the channels to prevent passage of the colonic effluent through a selected channel.

A colon cleanliness indicating system comprises the colon cleanliness indicating device, and electronic means for visualizing the indicating section and for outputting in response an indication that is representative of a degree of colon cleanliness.

In one embodiment, the electronic means comprises a terminal device configured to capture an image of the indicating section, and an optical meter in data communication with said terminal device for receiving said captured image, measuring optical properties of said captured image and for outputting in response the degree of colon cleanliness.

The terminal device may be a mobile device having a camera and a processor on which is running an application, said application being configured to provide instructions to a patient regarding a colon cleanliness assessing operation; display a request to direct the camera to the indicating section and to capture an image of the received colonic effluent; transmit the captured image to the optical meter; receive from the optical meter data indicative of the degree of colon cleanliness; and provide instructions to the patient, in response to the data received from the optical meter, whether an additional bowel preparation needs to be ingested.

In one aspect, the optical meter is a spectrophotometer.

In one embodiment, the system further comprises a support member for the indicating section when loaded with colonic effluent, wherein the electronic means comprises a light source for generating a light beam that is adapted to impinge on the indicating section, an optical meter for measuring optical properties of the light after interacting with the colonic effluent, and a processor-equipped terminal device for analyzing data generated by the optical meter in order to assess a degree of colon cleanliness.

In one aspect, the system further comprises a controlled indicator in data communication with the terminal device which is activated in response to a determination made by the terminal device that an additional bowel preparation needs to be ingested. The indicator may be an enunciator or a LED lamp.

DETAILED DESCRIPTION OF THE INVENTION

The present invention is a toilet-secured device for facilitating objective assessment of a degree of colon cleanliness prior to undergoing a colonoscopy examination. The degree of colon cleanliness, after ingesting a bowel preparation, is assessed by visualizing a sample of colonic effluent received by the device while remaining secured to the toilet, whether by eyesight or by electronic means. Thus, patient readiness for a colonoscopy examination may be assessed by a health professional.

The color of the visualized sample is representative of a degree of colon cleanliness. As described above, the colon must be free of solid matter to ensure efficacy of the colonoscopy examination, and therefore the colonic effluent should have a liquid consistency. A turbid and dark sample, however, is indicative that the colonic effluent contains thick particles. On the other hand, a clear and yellow sample is indicative of patient readiness for the colonoscopy examination. Different interim shades and levels of sample clarity represent different degrees of patient readiness for the colonoscopy examination.

Figure 1:
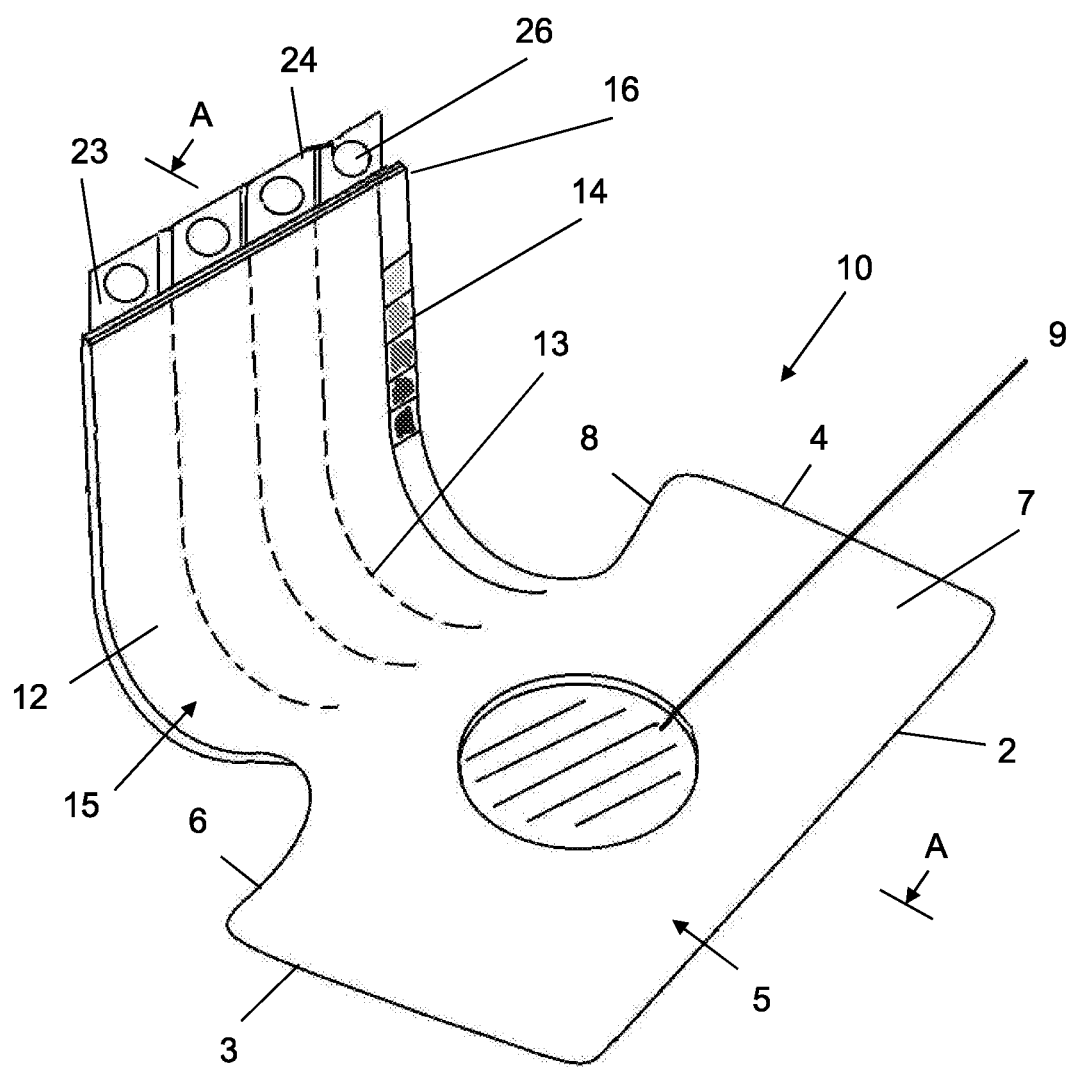
FIG. 1 is a schematic, perspective view from above of a colon cleanliness indicating device, according to one embodiment of the present invention, when unsecured but showing the angularly spacing of the indicating section with respect to the receiving section.

FIG. 1 illustrates the colon cleanliness indicating device, generally indicated by numeral 10, according to one embodiment of the present invention. Device 10 comprises a forward receiving section 5 for receiving colonic effluent and a rearward indicating section 15, generally angularly spaced with respect to receiving section 5, e.g. substantially vertically oriented, for indicating the degree of colon cleanliness. Device 10 is generally monolithic such that receiving section 5 and indicating section 15 are fabricated from the same material, preferably a transparent or translucent plastic, although each of receiving section 5 and indicating section 15 may be fabricated from different materials and coextensively joined together.

Receiving section 5 is configured by a wide-area, toilet-secured expanse 7 in which a receptacle 9 for the colonic effluent is downwardly recessed within a central region thereof. Receiving section 5 is shown to be rectangular with forward edge 2, side edges 3 and 4, and rear edges 6 and 8 extending from the end of a corresponding side edge to the end of a corresponding edge of indicating section 15; although any other receiving section shape is also in the scope of the invention. Receptacle 9 is shown to have an exemplary circular shape.

Indicating section 15 is narrower than receiving section 5, and is formed with one or more channels 12 in fluid communication with receptacle 9, through which colonic effluent is flowable and by which the sample may be visualized. Indicating section 15 may be provided with a color scale 14 to compare the color of the visualized sample with a range of reference colors displayed on the scale.

As referred to herein, the directional terms "forward" and "rearward" indicate the relative location of a corresponding section with respect to a user of device 10 when in a sitting position, although the corresponding section may be oriented in other ways when device 10 is unattached to a toilet.

Figure 2:
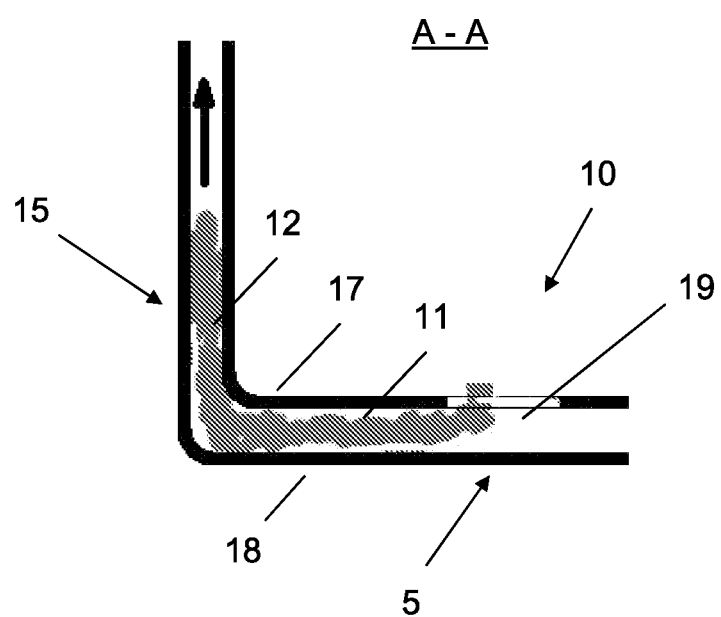
FIG. 2 is a cross sectional view of the device of FIG. 1, cut along plane A-A.

As shown in FIG. 2, both receiving section 5 and indicating section 15 of device 10 are made from two layers 17 and 18. Outer layer 17 is formed with an aperture 19 to define an opening of the colonic effluent receptacle.

While the two layers 17 and 18 are connected together in the portion of receiving section 5 forwardly of aperture 19, they are separated in the portion of receiving section 5 rearwardly of aperture 19 and throughout the lengthwise dimension of indicating section 15 to form a narrow void space therebetween of approximately 0.25 mm to define channel 12, for example ranging from 0.15-0.30 mm. The two layers 17 and 18 are also connected together in the portions of receiving section 5 that are laterally spaced from aperture 19.

The narrow void space facilitates capillary action therethrough following discharge of colonic effluent 11 into aperture 19. Capillary action results from the ability of the liquid content of the colonic effluent to flow lengthwise along the narrow gap of channel 12 due to the combination of adhesive forces between the liquid and one of the layers 17 and 18 and of surface tension of the liquid, when the gap is sufficiently small.

Since the two layers 17 and 18 are unseparated in the portions of receiving section 5 forwardly and laterally spaced from aperture 19, the received colonic effluent is urged to flow lengthwise by capillary action through a channel 12 to indicating section 15. The dimensions of the device may be customized according to the material from which it is fabricated, the width of the void space, the age or gender of the patient providing the sample, and any other relevant parameter.

It will be appreciated that receiving section 5 may be configured with a single layer in the portions thereof forwardly and laterally spaced from aperture 19, to urge the flow of received colonic effluent by capillary action through a channel 12 to indicating section 15.

Referring back to FIG. 1, indicating section 15 may be partitioned, to define a plurality of laterally adjacent channels 12. Each partition 13 between adjacent channels 12 may be formed by connecting the two layers along the entire length of indicating section 15 and the rearward portion of receiving section 5 to receptacle 9 by means well known to those skilled in the art, such as welding, heat sealing and adhesion. The partitions 13 also serve to add rigidity to receiving section 5 and indicating section 15.

An insert 23 is insertable within each channel 12, to prevent passage of colonic effluent through a channel when unwanted. Insert 23 occupies substantially the entire thickness of a corresponding channel 12, and may be movably sandwiched between the two device-defining layers during fabrication of device 10. To further ensure occlusion of a channel by an insert, a receptacle-facing end of an insert may be configured with a widened portion. The widened portion may comprise one or more elements which are coplanar or curved in such a way to occlude the receptacle-facing end of the corresponding channel, particularly an interspace between the main body of an insert and a channel wall, such as a partition or a portion of one of layers from which the device is fabricated, without occluding an adjacent channel. Insert 23 may be made from the same material as the material of receiving section 5 and indicating section 15, or from a different material.

A finger accessible tab 24, which may be formed with an opening 26 through which a finger is introducible to facilitate removal of the insert from the corresponding channel 12, may protrude from the terminal end 16 of the corresponding channel.

By selectively preventing flow of colonic effluent through a channel 12 by use of a corresponding insert 23, device 10 is advantageously able to be reusable. Prior to performing a colon cleanliness assessing operation, an insert 23 is removed from a selected channel 12 while the other channels remain occluded by the corresponding inserts. Thus after a sample is received, the colonic effluent flows by capillary action only through the selected channel from which the insert was removed. The color of the sample is then visualized via indicating section 15 and compared to the colors shown on color scale 14, by the patient or by a health professional. If the displayed color indicates that the patient is not yet ready for the colonoscopy examination, the receptacle is cleaned in preparation for a subsequent colon cleanliness assessing operation whereby the aforementioned method is repeated and the colonic effluent flows through more than one channel.

Figure 3:
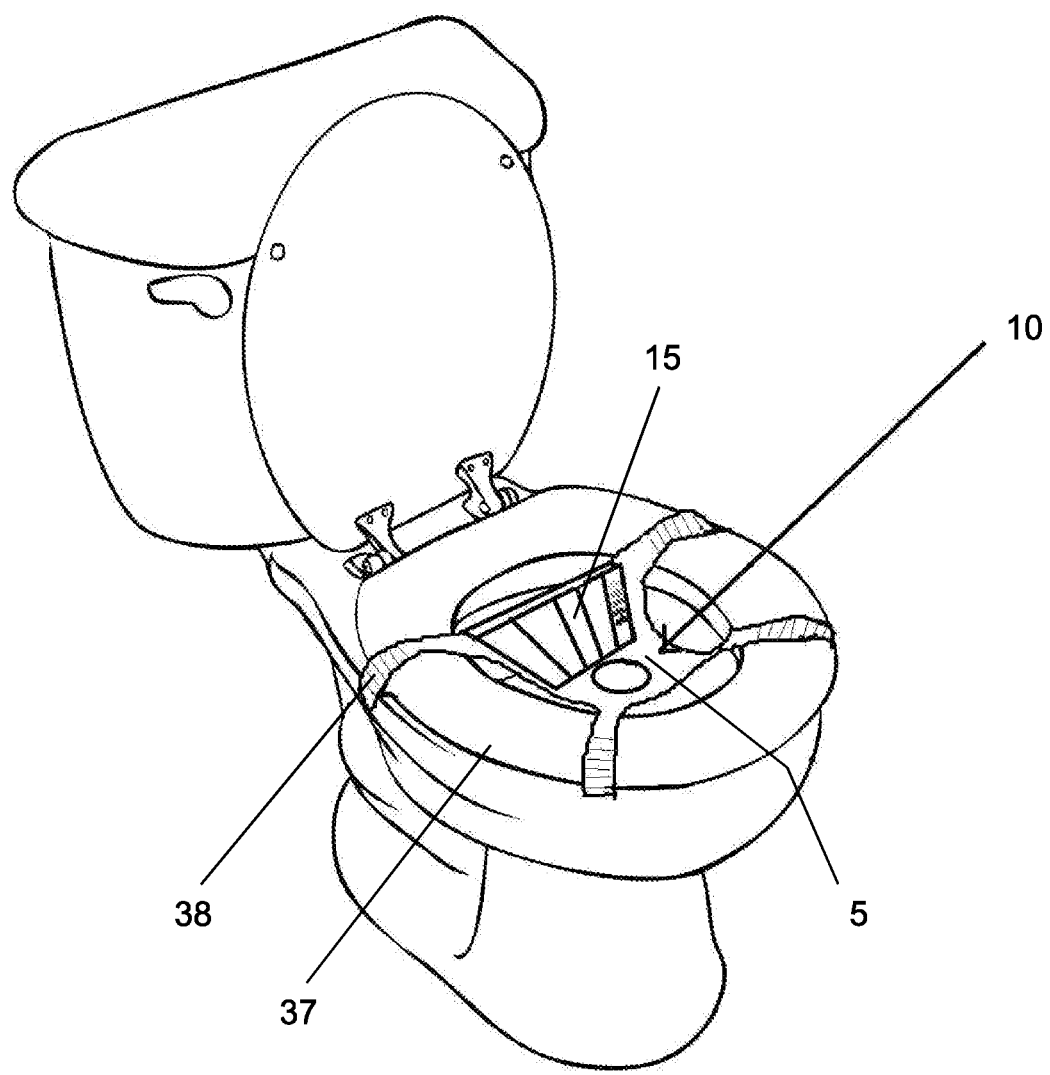
FIG. 3 is a perspective view of an arrangement for securing the device of FIG. 1 to a toilet.

FIG. 3 illustrates one arrangement for securing device 10 to a toilet 35. A plurality of straps 38 connected to device 10, for example two straps connected to receiving section 5 and two straps connected to indicating section 15, or four straps connected to receiving section 5, are each caused to loop around by a single turn, and be weighted down by, the sitting surface of annular toilet seat 37. Receiving section 5 is therefore positioned above the water level within the toilet bowl, and is also sufficiently stabilized to be able to receive a sample without sagging.

Figure 4:
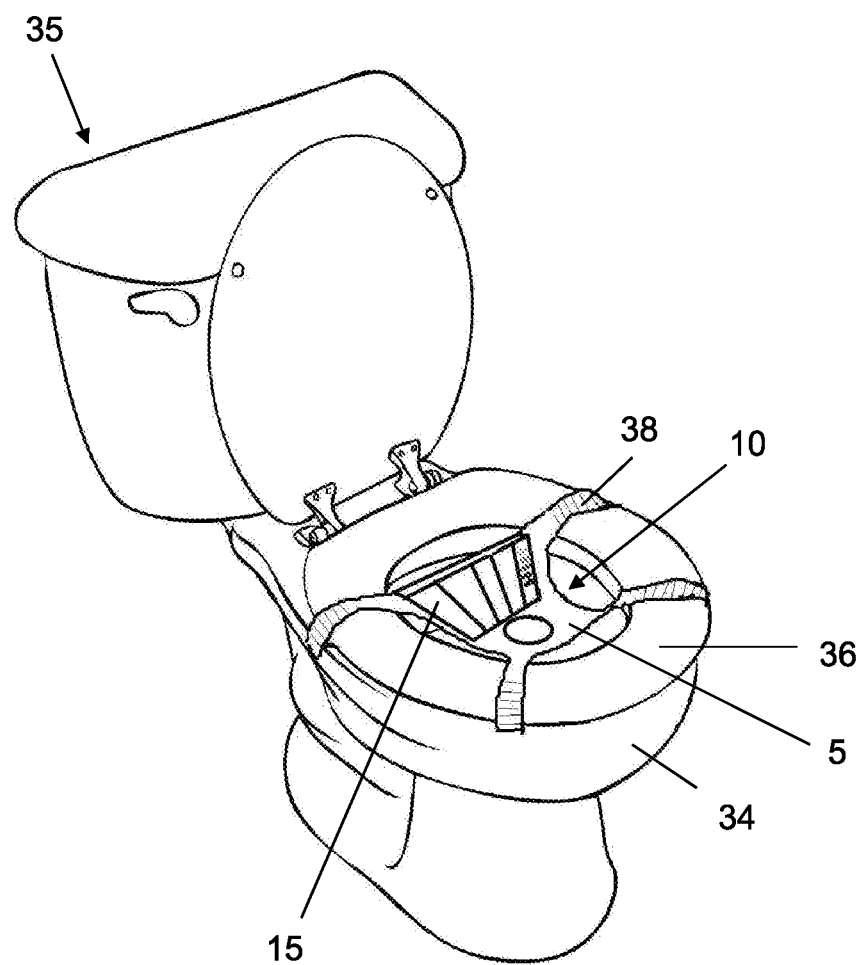
FIG. 4 is a perspective view of another arrangement for securing the device of FIG. 1 to a toilet.

FIG. 4 illustrates another arrangement for securing device 10 to a toilet 35. A plurality of straps 38, e.g. four straps, connected to receiving section 5 are caused to embrace toilet bowl rim 36. Afterwards, the toilet seat is pivoted to weight down the embraced straps and to prevent them from moving, while positioning receiving section 5 above the water level within toilet bowl 34. At the same time, indicating section 15 is able to be inserted through the small gap between the toilet seat and toilet seat cover while being substantially vertically oriented, so as to be protected from being soiled and to be positioned in a highly visible location.

The color of the sample may be visualized by eyesight or by electronic means, in conjunction with device 10 or with another type of device for assessing colon cleanliness prior to performance of a colonoscopy.

Figure 5:
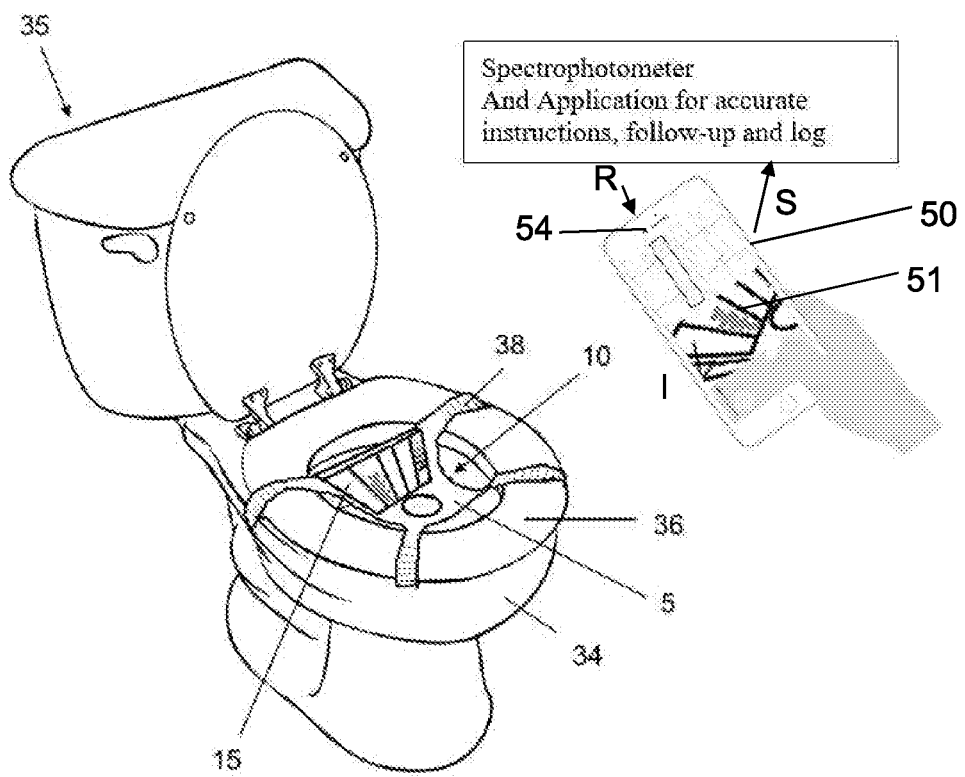
FIG. 5 is a schematic illustration of an embodiment of a system for electronically assessing a degree of colon cleanliness.

FIG. 5 illustrates a system 60 for electronically assessing a degree of colon cleanliness, as well as documenting the current degree of colon cleanliness and informing a user whether an additional colon cleanliness assessing operation is needed. System 60 is adapted for both home use and use at a health clinic.

System 60 comprises a camera-equipped mobile device 50, such as a smartphone, and an optical meter 64, such as a spectrophotometer, in data communication with mobile device 50.

An application 51, such as a spectrometer application, is running on the processor of mobile device 50, and is configured to verify user compliance with the colonoscopy preparation instructions and provide instructions to the user regarding an additional colon cleanliness assessing operation. For example, application 51 displays a request, when mobile device 50 is held by the user, to direct the schematically illustrated camera 54 to the indicating section 15 of device 10 and to capture an image of the given colonic effluent. After image I is captured, the application causes the captured image to be transmitted to optical meter 64 by signal S, whereupon optical meter 64 analyzes the acquired image. Following the analysis, optical meter 64 transmits a return signal R to mobile device 50, which is provided with data that is indicative of the degree of colon cleanliness. In response to the received data, application 51 indicates the degree of colon cleanliness related to the colonic effluent and provides instructions to the user, as to whether an additional bowel preparation needs to be ingested. The application may also save the received data, for use in future documentation.

Figure 6:
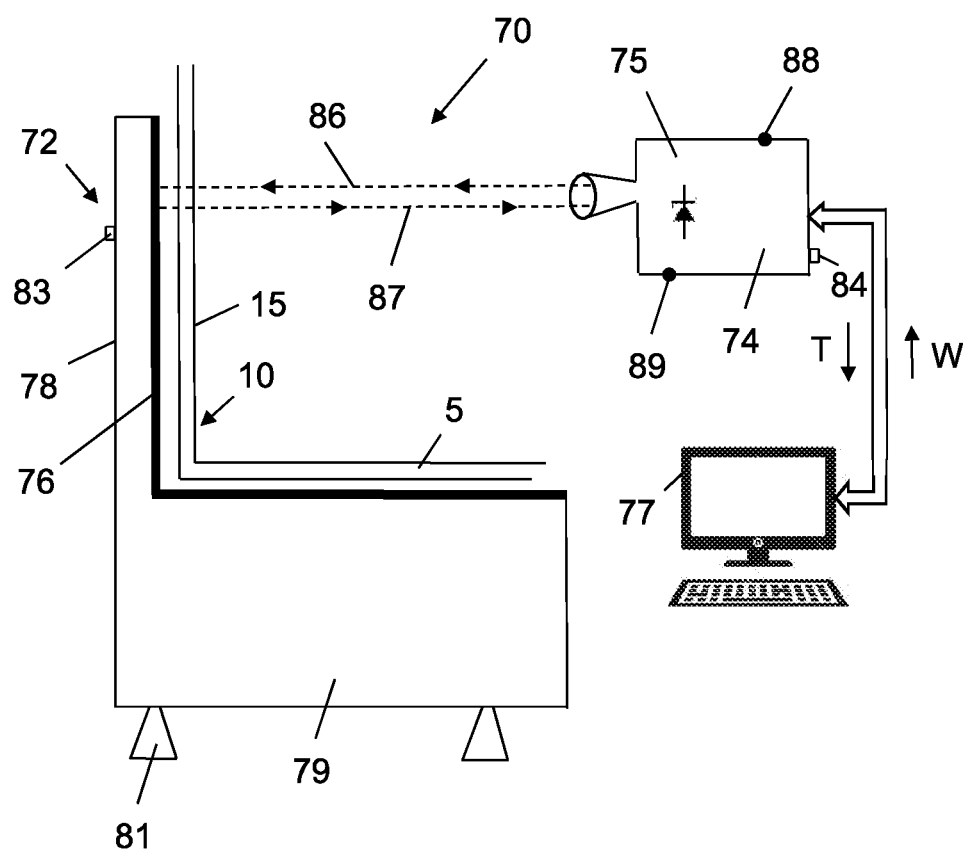
FIG. 6 is a schematic illustration of another embodiment of a system for electronically assessing a degree of colon cleanliness, showing a holder for the device of FIG. 1 in side view.

FIG. 6 illustrates another system 70 for electronically assessing a degree of colon cleanliness, which is generally adapted for use at a health clinic.

System 70 comprises a holder 72, or otherwise a support member, for a device 10 loaded with colonic effluent, a light source 74 which may be combined with an optical meter, and a processor-equipped terminal device 77, such as a personal computer, tablet or smartphone, for analyzing data generated by the optical meter in order to assess the degree of colon cleanliness. The optical meter may be a spectrophotometer.

Holder 72, which may be L-shaped and configured with two substantially mutually perpendicular surfaces 78 and 79 to support the similarly shaped colon cleanliness indicating device 10, is provided with a plurality of supporting legs 81 in order to be positioned on an underlying floor. Substantially vertical surface 78 extends to a height substantially equal to that of indicating section 15. A reflective layer 76 is applied to surface 78, and may also be applied to surface 79. Alternatively, a mounting element 83 may be connected to substantially vertical surface 78 for mounting on a wall surface. If so desired, surfaces 78 and 79 may be angularly spaced by any other suitable angle which substantially corresponds to the angular spacing between receiving section 5 and indicating section 15 of device 10. Accordingly, holder 72 and light source 74 may be permanently mounted at a health clinic, such as within a lavatory, for the convenience of patients located at a health clinic prior to undergoing a colonoscopy examination who would like to be informed whether an additional bowel preparation needs to be ingested.

Light source 74, by means of circuitry 75, is configured to generate a light beam 86, which may be monochromatic or non-coherent light, being directed at surface 78 of holder 72 and at indicating section 15 of device 10 when positioned in supporting relation with holder 72, preferably substantially perpendicular thereto. Support means 84 provided with light source 74, such as a mounting element or a set of legs, ensure that light beam 86 will be directed at surface 78. Following generation of radiation beam 86 in response to depressing activation button 88, a reflected beam 87 is reflected from reflective layer 76 and is received by the optical meter. The intensity of light received by the optical meter is dependent on the optical properties of radiation beam 86, the distance between light source 74 and reflective layer 76, the physical properties of reflective layer 76, and the opacity of indicating section 15 due to the influence of the colonic effluent received therein.

Data generated by the optical meter is transmitted by a signal T to, and analyzed by, terminal device 77, to determine the degree of colon cleanliness. A return signal W is transmitted to light source 74, which is provided with data that is indicative of the degree of colon cleanliness. In response to return signal W, circuitry 75 activates indicator 89 to indicate the degree of colon cleanliness and whether an additional bowel preparation needs to be ingested. Indicator 89 may be an enunciator for generating a first audible sound when it is determined that the colon is sufficiently clean and a second audible sound when it is determined that an additional bowel preparation needs to be ingested. Alternatively, indicator 89 may be a LED lamp that is illuminated by a first light signal when it is determined that the colon is sufficiently clean and by a second light signal when it is determined that an additional bowel preparation needs to be ingested.

Figure 7:
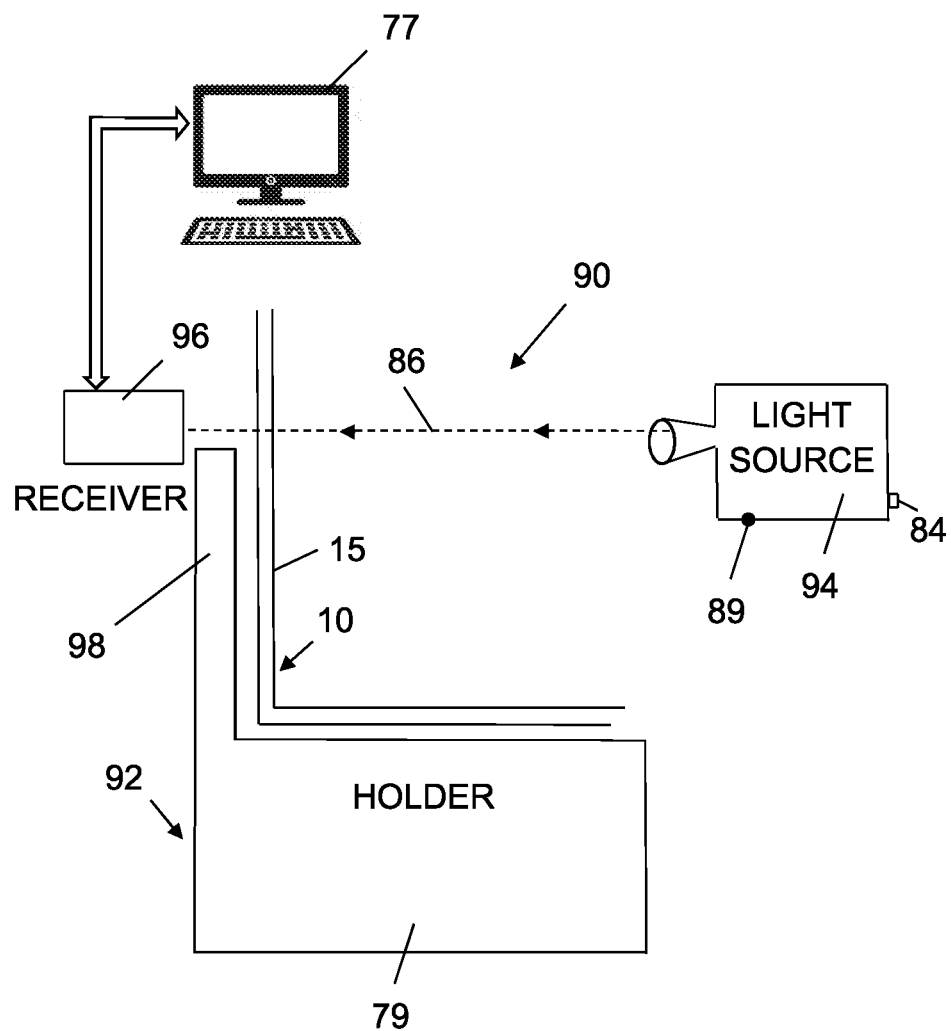
FIG. 7 is a schematic illustration of another embodiment of a system for electronically assessing a degree of colon cleanliness, showing a holder for the device of FIG. 1 in side view.

In system 90 of FIG. 7, which is similar to system 70 of FIG. 6, substantially vertical surface 98 of holder 92 is significantly shorter than indicating section 15, yet is sufficiently high and sturdy to support the indicating section. Light source 94 is positioned by mounting element 84 such that light beam 86, when generated thereby, will propagate above substantially vertical surface 98 of holder 92 and impinge on the portion of indicating section 15 protruding above surface 98. The optical properties of light beam 86 change as the light interacts with the colonic effluent while passing through indicating section 15. The light beam exiting indicating section 15 is received by optical meter 96, which is located at an opposite side of indicating section 15 than light source 94. Terminal device 77 analyzes the data generated by optical meter 96 to determine the degree of colon cleanliness. Indicator 89 may be activated by terminal device 77 when it is determined that the colon is not sufficiently clean and that an additional bowel preparation needs to be ingested.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:
1. A colon cleanliness indicating device, comprising
 a) a forward toilet-secured receiving section configured with a recessed receptacle for receiving colonic effluent, and
 b) a rearward indicating section for indicating a degree of colon cleanliness, wherein said indicating section is formed with one or more channels in fluid communication with said receptacle through which said received colonic effluent is flowable and by which said received colonic effluent is visualized in order to assess a degree of colon cleanliness,
wherein said indicating section is angularly spaced with respect to said receiving section and is substantially vertically oriented, and each of the one or more channels is configured with an internal gap of a sufficiently small dimension to induce flow of said received colonic effluent therethrough by capillary action.

2. The device according to claim 1, wherein the indicating section is made of transparent or translucent material to facilitate visualization of the induced-flow colonic effluent.

3. The device according to claim 2, wherein the indicating section is provided with a color scale to facilitate comparison of a color of the visualized induced-flow colonic effluent with a range of reference colors displayed on the scale.

4. A colon cleanliness indicating device, comprising
 a. a forward toilet-secured receiving section configured with a recessed receptacle for receiving colonic effluent, and
 b. a rearward indicating section for indicating a degree of colon cleanliness, wherein said indicating section is formed with one or more channels in fluid communication with said receptacle through which said received colonic effluent is flowable and by which said received colonic effluent is visualized in order to assess a degree of colon cleanliness,
wherein each of the one or more channels is made from two separated material layers, and one of said two layers is formed with an aperture to define an opening of the colonic effluent receptacle.

5. The device according to claim 4, wherein the two layers are unseparated within the receiving section forwardly of the aperture.

6. The device according to claim 5, wherein the two layers are also unseparated within portions of the receiving section that are laterally spaced from the aperture.

7. The device according to claim 4, wherein the receiving section is made of a single material layer forwardly and laterally of the aperture.

8. The device according to claim 4, wherein the indicating section is partitioned to define a plurality of laterally adjacent channels.

9. The device according to claim 8, wherein each partition between a pair of the laterally adjacent channels is connected to the two layers along the entire length of the indicating section and along a rearward portion of the receiving section to an edge of the aperture.

10. The device according to claim 9, further comprising one or more inserts, each of said inserts being insertable within a corresponding one of the channels to prevent passage of the colonic effluent through a selected channel.

11. The device according to claim 10, wherein a receptacle-facing end of the insert is configured with a widened portion to occlude a receptacle-facing end of the corresponding channel.

12. The device according to claim 10, wherein the insert is configured with a finger accessible tab to facilitate removal of the insert from the corresponding channel.

13. A colon cleanliness indicating system, comprising:
a) a colon cleanliness indicating device comprising a forward toilet-secured receiving section configured with a recessed receptacle for receiving colonic effluent, and
a rearward indicating section for indicating a degree of colon cleanliness,
wherein said indicating section is formed with one or more channels in fluid communication with said receptacle through which said received colonic effluent is flowable and by which said received colonic effluent is visualized in order to assess a degree of colon cleanliness; and
b) electronic means for visualizing the said section and for outputting in response an indication that is representative of a degree of colon cleanliness,
wherein said electronic means comprises a terminal device configured to capture an image of said indicating section, and an optical meter in data communication with said terminal device for receiving said captured image, measuring optical properties of said captured image and for outputting in response the degree of colon cleanliness,
wherein said terminal device is a mobile device having a camera and a processor on which is running an application, said application being configured to:
a. provide instructions to a patient regarding a colon cleanliness assessing operation;
b. display a request to direct the camera to said indicating section and to capture an image of said received colonic effluent;
c. transmit the captured image to the optical meter;
d. receive from the optical meter data indicative of the degree of colon cleanliness; and
e. provide instructions to the patient, in response to the data received from the optical meter, whether an additional bowel preparation needs to be ingested.

14. The system according to claim 13, wherein the optical meter is a spectrophotometer.

15. A colon cleanliness indicating system, comprising:
a) a colon cleanliness indicating device comprising a forward toilet-secured receiving section configured with a recessed receptacle for receiving colonic effluent and a rearward indicating section for indicating a degree of colon cleanliness, wherein said indicating section is formed with one or more channels in fluid communication with said receptacle through which said received colonic effluent is flowable and by which said received colonic effluent is visualized in order to assess a degree of colon cleanliness;
b) electronic means for visualizing said indicating section and for outputting in response an indication that is representative of a degree of colon cleanliness; and
c) a support member for the indicating section when loaded with colonic effluent, wherein said electronic means comprises a light source for generating a light beam that is adapted to impinge on said indicating section, an optical meter for measuring optical properties of the light after interacting with said received colonic effluent, and a processor-equipped terminal device for analyzing data generated by the optical meter in order to assess a degree of colon cleanliness.

16. The system according to claim 15, further comprising a controlled indicator in data communication with the terminal device which is activated in response to a determination made by the terminal device that an additional bowel preparation needs to be ingested.

17. The system according to claim 16, wherein the indicator is an enunciator or a LED lamp.

18. The system according to claim 4, wherein the indicating section is angularly spaced with respect to the receiving section and is substantially vertically oriented, and wherein each of the one or more channels is configured with an internal gap of a sufficiently small dimension to induce flow therethrough of the received colonic effluent by capillary action.

19. The system according to claim 18, wherein the indicating section is made of transparent or translucent material to facilitate visualization of the induced-flow of colonic effluent.

* * * * *